US011475625B1

(12) United States Patent
Douglas

(10) Patent No.: US 11,475,625 B1
(45) Date of Patent: Oct. 18, 2022

(54) METHOD AND APPARATUS FOR GENERATING A PRECISION SUB-VOLUME WITHIN THREE-DIMENSIONAL IMAGE DATASETS

(71) Applicant: Robert Edwin Douglas, Winter Park, FL (US)

(72) Inventor: Robert Edwin Douglas, Winter Park, FL (US)

(73) Assignee: RED PACS, LLC, Winter Park, FL (US)

( * ) Notice: Subject to any disclaimer, the term of this patent is extended or adjusted under 35 U.S.C. 154(b) by 169 days.

(21) Appl. No.: 16/927,886

(22) Filed: Jul. 13, 2020

Related U.S. Application Data

(63) Continuation-in-part of application No. 16/879,758, filed on May 21, 2020, now Pat. No. 10,776,989, and a continuation-in-part of application No. 16/842,631, filed on Apr. 7, 2020, now Pat. No. 11,003,342, and a continuation-in-part of application No. 16/683,256, filed on Nov. 13, 2019, now Pat. No. 11,158,045, and a continuation-in-part of application No. 16/594,139, filed on Oct. 7, 2019, now Pat. No. 10,893,844.

(60) Provisional application No. 62/985,363, filed on Mar. 5, 2020.

(51) Int. Cl.
*G06T 15/08* (2011.01)
*G06T 19/00* (2011.01)
*G06K 9/62* (2022.01)
*G06F 3/01* (2006.01)
*G06T 7/11* (2017.01)

(52) U.S. Cl.
CPC .............. *G06T 15/08* (2013.01); *G06F 3/013* (2013.01); *G06K 9/6217* (2013.01); *G06T 7/11* (2017.01); *G06T 19/006* (2013.01); *G06T 2200/04* (2013.01); *G06T 2210/41* (2013.01); *G06V 2201/03* (2022.01)

(58) Field of Classification Search
CPC ................... G06T 7/0012; G06T 15/08; G06T 2207/10112; G06T 2207/30068; G06T 2207/30096; G06T 19/006; G06T 17/10; G06T 19/20; G06T 2207/10081; G06T 2210/41; G06T 7/11; G06T 2200/04; G06T 2207/10088; G06T 2207/20084; G06F 3/013; G06V 40/18
See application file for complete search history.

(56) References Cited

U.S. PATENT DOCUMENTS

2020/0359981 A1 * 11/2020 Straka .................... A61B 6/032

* cited by examiner

Primary Examiner — Ross Varndell

(57) ABSTRACT

A method, apparatus and computer program for generating a sub-volume within a 3D dataset in a consistent, repeatable fashion. To accomplish this, geometric object(s) (e.g., 2D planes) are placed at precise anatomic landmarks with precise sizes and orientations. This serves to divide the 3D object into multiple parts (e.g., a first portion of the 3D volume has a first set of voxels and a second portion of the 3D volume has a second set of voxels). This process continues as multiple additional geometric objects are placed so that certain features of the 3D dataset can be extracted (i.e., shown with the best viewing settings). This process when used in conjunction with a radiologist's checklist enables efficient volume-by-volume viewing.

20 Claims, 7 Drawing Sheets

400

| Checklist item | Digital geometric object(s) | Other visualization techniques implemented |
|---|---|---|
| Cerebral vasculature | 6 planes with anatomical landmarks identified by AI algorithm, as disclosed in Figure 1 | Two different visual representation adjustment logics applied to different parts of the same segmented structure (e.g., Anterior cerebral arteries non-transparent and all other cerebrovascular structures transparent) |
| Craniocervical junction | Sphere of radius 5 cm placed on tip of dens | View points performed from 6 angles each at 7 cm from tip of dens (top, bottom, left, right, front, back) |

Figure 5

| Techniques for improving analysis of the sub-volume |
| --- |
| Stereoscopic rendering with voxel filtering |
| Stereoscopic rendering with convergence |
| Stereoscopic rendering on alternative headset displays |
| 3D volume cursor use |
| Interactive 3D volume cursor use |
| Double windowing techniques |
| Modified segmented structure techniques |
| Analyzing structures under different morphologic conditions |
| Smart scrolling |
| Eye tracking |
| Geo-registered tools and virtual tool box techniques |
| Prioritized volume rendering |
| Radiologist assisted machine learning |
| Flow visualization techniques |
| Automatic shape recognition technology |

Figure 6

Examples of digital geometric object
- a point in space (or a single voxel)
- a line (straight or curving)
- a plane (or a curving surface)
- a 3D object (such as a sphere, cube, cube-like structure or cone)

700

Examples of pre-selected anatomic landmarks
- specific spots on a bone (e.g., pterion of the calvarium)
- specific spots on the thyroid gland (e.g., anterior most portion of the isthmus)
- specific spots on the liver (e.g., falciform ligament)

701

Examples contents of sub-volumes
- An item on a radiologist's checklist (e.g. cerebrovasculature)
- An item that a surgeon is interested in looking at more closely (e.g., kidney which has suffered a laceration and surgeon needs to determine whether he / she can repair it or needs to perform a nephrectomy)

702

Examples of viewing of sub-volumes
- 2D monitor
- Extended reality display

703

Examples of usage of artificial intelligence in this process
- Anatomic landmark identification
- Determining optimal viewing angle
- Determine optimum implementation of multiple visual representation adjustment logic application (e.g., first image processing technique (non-transparent) is performed on the proximal third of the anterior cerebral artery, second image processing technique (50% transparent) is applied to the middle third of the anterior cerebral artery, third image processing technique (90% transparent) applied to the distal third of the anterior cerebral artery.

METHOD AND APPARATUS FOR GENERATING A PRECISION SUB-VOLUME WITHIN THREE-DIMENSIONAL IMAGE DATASETS

TECHNICAL FIELD

Aspects of this disclosure are generally related to image processing.

BACKGROUND

A radiologist works with three-dimensional datasets to diagnose a wide range of pathologic conditions. Advanced visualization is useful because it can improve diagnostic accuracy.

SUMMARY

All examples, aspects, and features mentioned in this document can be combined in any technically conceivable way.

This patent provides a method, apparatus and computer program for generating a sub-volume within a 3D dataset in a consistent, repeatable fashion. To accomplish this, geometric object(s) (e.g., planes) are placed at precise anatomic landmarks with precise sizes and orientations. This serves to divide the 3D object into multiple parts (e.g., a first portion of the 3D volume has a first set of voxels and a second portion of the 3D volume has a second set of voxels). This process continues as multiple additional geometric objects are placed so that certain features of the 3D dataset can be extracted (i.e., shown with the best viewing settings). This process when used in conjunction with a radiologist's checklist enables efficient volume-by-volume viewing.

The preferred application of this technology is to improve visualization of complex anatomic structures by a radiologist. The preferred embodiment for this invention is creation of a sub-volume (e.g., a cubelike structure) within a three dimensional dataset (e.g., solid object) using recognizable landmarks for construction of six planes which intersect to form the cubelike structure and then cropping and removing the material of the solid which is external to the cubelike structure so that only the cubelike structure remains. As an example, suppose the solid object were a skull whose voxels were derived from medical images (e.g., MRI, CT, PET) as described in U.S. Pat. No. 8,384,771, METHOD AND APPARATUS FOR THREE DIMENSIONAL VIEWING OF IMAGES, which is incorporated by reference. Then, application of landmarks and crop planes would be as follows: the superior crop plane was 2 cm above the corpus callosum. The inferior crop plane was 1 cm below the level of the foramen magnum. The lateral crop planes were 1 cm medial to the squamosal portion of the temporal bones. The anterior and posterior crop planes were the midpoint of the cribriform plate and midpoint of the foramen magnum, respectively. To continue with this example, some embodiments would not remove the material external to the structure but, would instead, change the transparency of the material external to the cubelike structure (i.e., the skull/eye sockets/nose/ears) would be 'see through' and the cubelike structure would be fully visible. In some embodiments a Cartesian coordinate system could be virtually affixed to the cubelike structure which facilitate reporting the location of salient features.

The preferred embodiment is for the anatomic landmarks to be pre-selected. For example, for a given item on a radiologist's checklist (e.g., cerebrovasculature), the landmarks as described above are pre-selected and inputted into the algorithm. This enables the process to be repeatable and reproducible over the same patient and over multiple patients.

The preferred embodiment is also for the geometric objects to be pre-selected. In the example of the cerebrovasculature, for a given item on a radiologist's checklist (e.g., cerebrovasculature), the geometric objects (e.g., 2D planar slices) are also pre-selected and inputted into the algorithm. This enables the process to be repeatable and reproducible over the same patient and over multiple patients.

In some embodiments a three-dimensional (3D) cursor would be inserted within the cubelike structure as described in U.S. Pat. No. 9,980,691, METHOD AND APPARATUS FOR THREE DIMENSIONAL VIEWING OF IMAGES, which is incorporated by reference. To continue to build on the medical example described above, suppose a filtering process was applied to the material within the cubelike structure such that all material except the vascular structure was removed. Then, further suppose the purpose of the user was to detect any aneurysms, if present. Then, given an aneurysm were present in the cubelike structure, the user could re-size and re-orient the 3D cursor in order to encapsulating the aneurysm and only the aneurysm. In some embodiments, the volume of the re-sized 3D cursor would be computed by counting the number of voxels within the 3D cursor. (Note that the volume of a voxel would have been determined when the process of U.S. Pat. No. 8,384,771, METHOD AND APPARATUS FOR THREE DIMENSIONAL VIEWING OF IMAGES, which is incorporated by reference was applied.) Under this embodiment the dimensions and orientation of the 3D cursor with respect to the Cartesian coordinate system could be recorded and inserted into a report about the cubelike structure. In some embodiments, trigger phrases could be used that will insert some expanded preselected text into the report to speed writing. For example, the abbreviation CA could be verbalized and, inserted into the report would be the phrase "cerebral aneurysm located at coordinate X, Y, Z in the anterior cerebral artery". (See later embodiment which brings in artificial intelligence to name blood vessels in the brain.)

In some embodiments, the cubelike structure could be viewed using an extended reality headset (or other device) capable of displaying stereoscopic 3D images. To continue the above example, suppose stereoscopic 3D viewing of the cubelike structure which was within the skull (i.e., the brain which had undergone a segmentation and filtering algorithm optimized for cerebrovasculature). The context for this example would be a medical facility and the user would be a radiologist. Under these conditions, the viewing procedure could be repeated throughout the day. In some embodiments, standardized settings could expedite the process. Such expediting measures could include, but not be limited to: display of the cerebrovasculature could be at an optimized viewing distance as seen through the head display unit; preferred rotation angles could be triggered by verbal, keyboard, hand control unit; and a set of preferred observation points could be specified for optimized viewing perspective of the cerebrovasculature. In some embodiments, the display could involve multiple images which could include but, would not be limited to: a zoomed in view of some feature together with the larger view of the cubelike structure; a portrayal of the observation point currently in use with respect to the cubelike structure together with the change the transparency of the material external to the cubelike structure and cubelike structure from that observation point perspective superimposed on the current view to help orient the user; a side-by-side display of images taken at different times to see changes, if any (note: this particular side-by-side view could be accompanied by a table comparative volumes of respective aneurysms over time periods being considered); and a small version of the larger view with a transparent cone of the user's field of view from the current user's observation position superimposed on this larger view together with the current view. These are but a few of the combinations which are possible and encompassed in this patent.

In some embodiments, it may be useful to expand the distance between closely spaced items of interest. To continue with the example being used in previous paragraphs, blood vessels would be items of interest and, in certain parts of the brain, the blood vessels are very closely spaced. Further, because of their circuitous paths these blood vessels take, it is difficult to discern if abnormalities are present. Note that techniques for expansion were explained in U.S. patent application Ser. No. 16/195,251, INTERACTIVE VOXEL MANIPULATION IN VOLUMETRIC MEDICAL IMAGING FOR VIRTUAL MOTION, DEFORMABLE TISSUE, AND VIRTUAL RADIOLOGICAL DISSECTION, which is incorporated by reference. Note that through applying the segmentation process per U.S. Pat. No. 8,384,771, METHOD AND APPARATUS FOR THREE DIMENSIONAL VIEWING OF IMAGES, which is incorporated by reference. each individual blood vessel will be outlined. Then, from some central portion of the brain such as the Circle of Willis, the arteries could be spread out so that each artery could be viewed individually from spherically placed viewpoints without being occluded by other arteries. Connections from the Circle of Willis to the arteries could be shown on the display through techniques such as but, not limited to: adding false blood vessel segments with distinguishing markings or color; lines; a numbering system with the same numbers on both one end of the artery and on the Circle of Willis; transformable voxels that stretch allowing expansion. In this embodiment, the user could get a very clear picture of each artery without trying to unwind the 'Gordian Knot' of blood vessels.

In some embodiments, it may be useful to expand the volume of closely spaced items of interest and then reduce the viewer perspective as if the user was a small person in a big world. To continue with the example being used in previous paragraphs, blood vessels would be items of interest. And, in this embodiment, the blood vessels would appear virtually as a large pipeline whereas, the user would be small in comparison. The user could virtually fly around inside of this pipeline complex and inspect each pipe. Aneurysms would stand out as very large bulges in the pipe. The exact size and shape could be very accurately measured and described.

In some embodiments, it may be useful to use artificial intelligence (AI) to name each of the items of interest within the cubelike structure. To continue with the example being used in previous paragraphs, major blood vessels would be named after the brain and other non-vasculature structures had undergone a segmentation and filtering algorithm optimized for cerebrovasculature. In furthering this embodiment, then a set of vectors along blood vessel path could be created. Additionally, vectors orthogonal to the blood path vectors could be created to measure the diameter of the blood vessel along its path. In furthering this embodiment, suspect points could be identified where diameter increases which would help the user detect a possible aneurysm. The blood vessel diameter could be measured radially from the center of the blood vessel to the walls in multiple directions (e.g., 360 radial measurements for the 360 degrees of a cross-section of the blood vessel). A list of suspect points could be displayed which the user could click through and a zoomed in image of that region could be displayed and associated system capabilities such as rotation of that region be invoked. This embodiment would be helpful in improving false positive/negative readings.

In some embodiments, it may be useful to selectively use transparency to help separate each of the items of interest within the cubelike structure. To continue with the example being used in previous paragraphs, all but one of the major blood vessels would undergo transparency after the brain had undergone a segmentation and filtering algorithm optimized for cerebrovasculature. This process would continue and in the next iteration, all blood vessels would undergo transparency but one—a different one. And, the sequence of iterations would continue until such time when all blood vessels had an opportunity to be the only blood vessel displayed that had not undergone transparency. In furthering this embodiment, some method (e.g., some marking) would be used to connote progress of the review to help ensure all vessels have been viewed. This embodiment could also include a travelling point (or arrow, etc.) along blood vessel to eliminate saccadian eye movement which skips from one point to another possible missing important features rather than continuous eye movement where the eye follows the travelling point. This embodiment would be very useful to declutter the overlapping/interwoven blood vessels.

In some embodiments, it may be useful to selectively use automatic shape recognition technology to help detect key features of the items of interest within the cubelike structure. To continue with the example being used in previous paragraphs, automatic shape recognition technology could be applied to regions surrounding each of the identified suspect points after the brain had undergone a segmentation and filtering algorithm optimized for cerebrovasculature and after AI had identified the suspect points. In furthering this embodiment, the automatic shape recognition technology could be trained to detect balloons protruding from a normally rounded shape of an aneurysm. Note that these balloons can indicate a weak section in the lining of the aneurysm which could rupture and thus be lethal. Given that one of these balloons had been detected, this potentially dangerous condition would be highlight in some manner (e.g., blinking red color).

In some embodiments, it may be useful to use combinations of above embodiments to help detect and identify key features of the items of interest within the cubelike structure.

In the above embodiments, examples were given surrounding cerebral aneurysms (CA). Similar embodiments could be cerebral embolism (CE). As an example, whereas a tell-tale sign of a CA is an expanding diameter of a blood vessel, tell-tale sign of a CE could be a step change decreasing diameter of a blood vessel indicative of a clot blocking blood flow. A further example, if the user were trace along the within the blood vessel, data units (e.g., Hounsfield units) could be displayed. A blood clot has a different Hounsfield unit than normal blood and this change could indicate the presence of clot. As with a CA and a CE, similar embodiments could be applied in detection and classification of brain tumors. Whereas in a CA example automatic shape recognition technology, was invoked in an embodiment, similar technology could be applied to classify types of brain tumors and determine the type of brain tumor and the stage thereof. In other embodiments examples of CA, a 3D cursor encased the CA and the volume was computed. In a similar manned, the 3D cursor could encase the brain tumor and volume computed. This would also apply the measurements taken over time to quantify changes, if any, in the brain tumor.

In some embodiments, a unique sub-volume is generated for each item in the radiologist's checklist. For example, a first sub-volume with segmentation and filtering optimized for the cerebrovasculature is examined. Then, a second sub-volume with segmentation and filtering optimized for the right orbit. Then, a third sub-volume with segmentation and filtering is optimized for the left orbit. And so on. Thus, this process enables a volume-by-volume review for each item in the anatomic checklist.

Still other embodiments include a computerized device, configured to process all the method operations disclosed herein as embodiments of the invention. In such embodiments, the computerized device includes a memory system, a processor, communications interface in an interconnection mechanism connecting these components. The memory system is encoded with a process that provides steps explained herein that when performed (e.g. when executing) on the processor, operates as explained herein within the computerized device to perform all of the method embodiments and operations explained herein as embodiments of the invention. Thus any computerized device that performs or is programmed to perform processing explained herein is an embodiment of the invention.

Other arrangements of embodiments of the invention that are disclosed herein include Software programs to perform the method embodiment steps and operations Summarized above and disclosed in detail below. More particularly, a computer program product is one embodiment that has a computer-readable medium including computer program logic encoded thereon that when performed in a computerized device provides associated operations providing steps as explained herein.

The computer program logic, when executed on at least one processor with a computing system, causes the processor to perform the operations (e.g., the methods) indicated herein as embodiments of the invention. Such arrangements of the invention are typically provided as Software, code and/or other data structures arranged or encoded on a computer readable medium such as an optical medium (e.g., CD-ROM), floppy or hard disk or other a medium such as firmware or microcode in one or more ROM or RAM or PROM chips or as an Application Specific Integrated Circuit (ASIC) or as downloadable software images in one or more modules, shared libraries, etc. The software or firmware or other Such configurations can be installed onto a computerized device to cause one or more processors in the computerized device to perform the techniques explained herein as embodiments of the invention. Software processes that operate in a collection of computerized devices, such as in a group of data communications devices or other entities can also provide the system of the invention. The system of the invention can be distributed between many software processes on several data communications devices, or all processes could run on a small set of dedicated computers, or on one computer alone.

It is to be understood that the embodiments of the invention can be embodied strictly as a software program, as Software and hardware, or as hardware and/or circuitry alone. Such as within a data communications device. The features of the invention, as explained herein, may be employed in data processing devices and/or Software systems for Such devices. Note that each of the different features, techniques, configurations, etc. discussed in this disclosure can be executed independently or in combination. Accordingly, the present invention can be embodied and viewed in many different ways. Also, note that this Summary section herein does not specify every embodiment and/or incrementally novel aspect of the present disclosure or claimed invention. Instead, this Summary only provides a preliminary discussion of different embodiments and corresponding points of novelty over conventional techniques. For additional details, elements, and/or possible perspectives (permutations) of the invention, the reader is directed to the Detailed Description section and corresponding figures of the present disclosure as further discussed below.

BRIEF DESCRIPTION OF THE FIGURES

The foregoing will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 5 illustrates examples of radiologist checklist items with associated digital geometric objects for sub-volume creation and subsequent visualization techniques implemented.

FIG. 6 illustrates a table highlighting techniques for improving analysis of the sub-volume.

FIG. 7 illustrates text boxes highlighting key aspects in this patent.

DETAILED DESCRIPTION

Figure 1A:
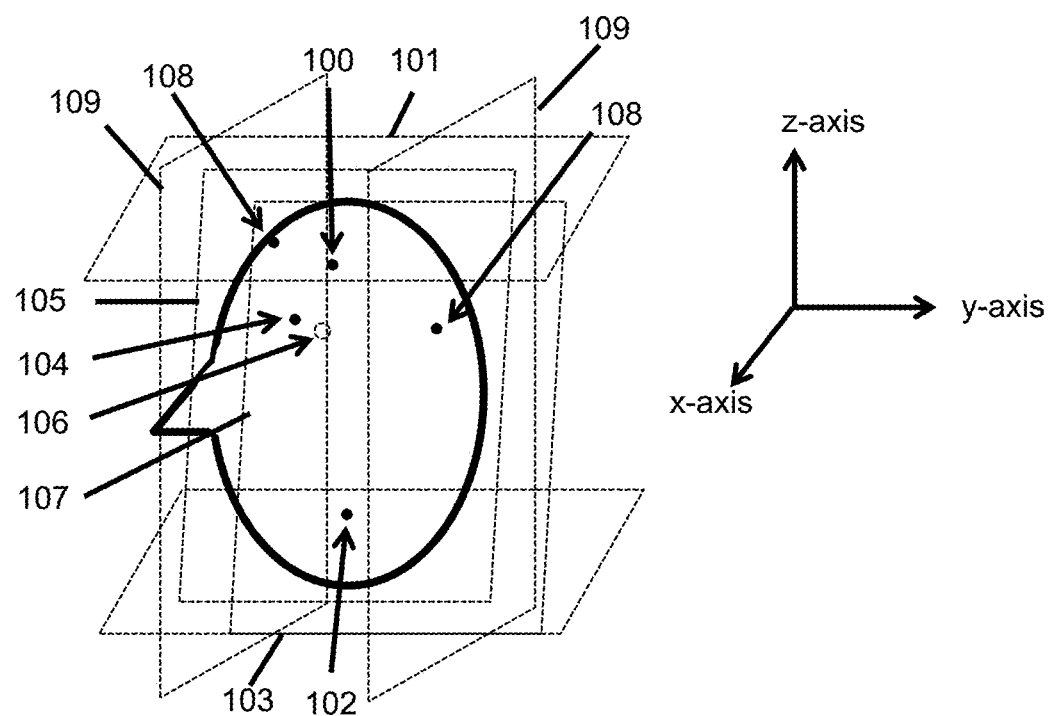
FIG. 1A illustrates the use of 6 planes defined by 6 anatomical landmarks to define the sub-volume of interest.

FIG. 1A illustrates the use of 6 planes defined by 6 anatomical landmarks to define the sub-volume of interest. X-axis, Y-axis and Z-axis are shown. Six planes surrounding the majority of the cerebrovasculature wherein the location of the planes is based on human landmarks and the intersection of these 6 planes would create a cubelike sub-volume. The landmarks are readily recognizable by one trained in the art. This has the advantage of the process being able to be replicated between users so that, from one user to another, the volume presented to the users would be consistent. Based on a consistent volume, the results from a review should be consistent. The preferred embodiment, however, is the use of an artificial intelligence algorithm to identify the anatomic landmarks and the associated geometric objects. 100 illustrates an anatomical landmark that is 1 cm inferior to the inner table of the calvarium at the vertex, which in this example is (250, 250, 500). 101 illustrates a geometrical object (e.g., a 2D plane) defined by point 100 and the plane defined by z=500. 102 illustrates an anatomical landmark that is 1 cm superior to the ophthesion of the calvarium at the vertex, which in this example is (250, 250, 50). 103 illustrates a geometrical object (e.g., a 2D plane) defined by point 102 and the plane defined by z=50. 104 illustrates an anatomical landmark that is 1 cm medial to the right pterion at the inner table of the calvarium, which in this example is (450, 250, 250). 105 illustrates a geometrical object (e.g., a 2D plane) defined by point 104 and the plane defined by x=450. 106 illustrates an anatomical landmark that is 1 cm medial to the left pterion at the inner table of the calvarium, which in this example is (50, 250, 250). 107 illustrates a geometrical object (e.g., a 2D plane) defined by point 104 and the plane defined by x=50. 108 illustrates an anatomical landmark that is the bregma at the inner table of the calvarium, which in this example is (250, 50, 550). 109 illustrates a geometrical object (e.g., a 2D plane) defined by point 104 and the plane defined by y=50. 110 illustrates an anatomical landmark that is the lambda at the inner table of the calvarium, which in this example is (250, 550, 250). 111 illustrates a geometrical object (e.g., a 2D plane) defined by point 104 and the plane defined by y=50. Thus, in this example 6 points are used as locations for 6 2D planes. These planes are used for the creation of a cubelike structure within a solid volume (i.e., a sub-volume) of the entire 3D dataset performed via cropping. Note that in the preferred embodiment, each plane is defined by at least one anatomic structure, which in the preferred embodiment the set of anatomic markers are pre-determined in accordance with the item on a radiologist's checklist. The intersection of these planes are positioned such that the majority of the cerebrovasculature is encased within these intersections. Note that the preferred embodiment is the alignment of the geo-metric objects with anatomic landmarks; however, other non-medical 3D datasets (e.g., voxelated datasets) could also be used. In these non-medical examples, the landmarks would not be human body anatomic sites, but would be landmarks in accordance with the type of dataset used.

Figure 1B:
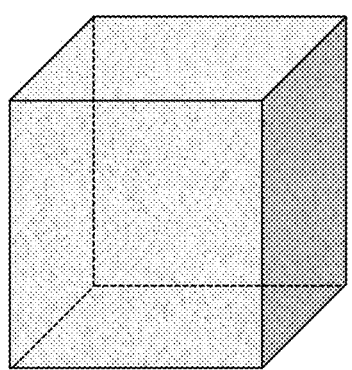
FIG. 1B illustrates the cubelike structure that remains after cropping those portions of the skull structure which are external to the enclosed volume.

FIG. 1B illustrates the cubelike structure that remains after cropping those portions of the skull structure which are external to the enclosed volume. Note that at this juncture, the voxels on the surface are illustrated.

Figure 1C:
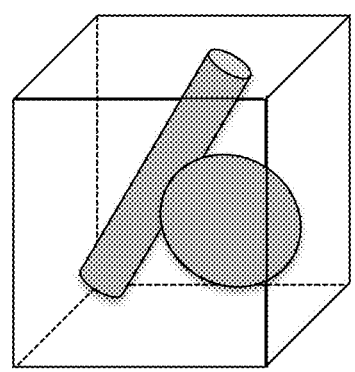
FIG. 1C illustrates applying segmentation and filtering to isolate key features within the cubelike sub-volume.

FIG. 1C illustrates applying segmentation and filtering to isolate key features within the cubelike sub-volume. For this particular example, the objective of the endeavor is to detect brain algorithms while using a true stereoscopic extended reality headset. The tissue remaining after the brain which had undergone a segmentation and filtering algorithm optimized for leaving only the cerebrovasculature.

Figure 2A:
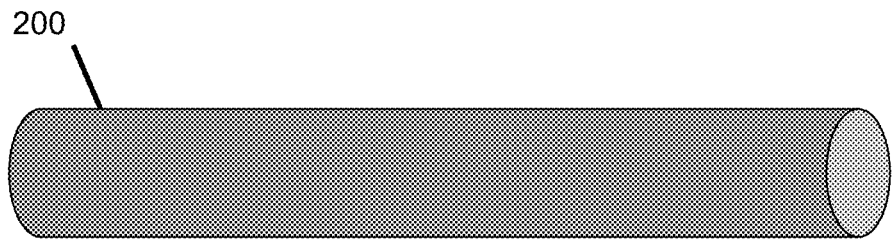
FIG. 2A illustrates segmented with a single visual representation adjustment logic applied to it.

FIG. 2A illustrates segmented with a single visual representation adjustment logic applied to it. 200 illustrates a vascular structure. Note that the entire vascular structure is shown with the same visual representation adjustment logic. Namely, since the entire blood vessel has similar data units (e.g., Hounsfield Units), the entire blood vessel is shown as gray.

Figure 2B:
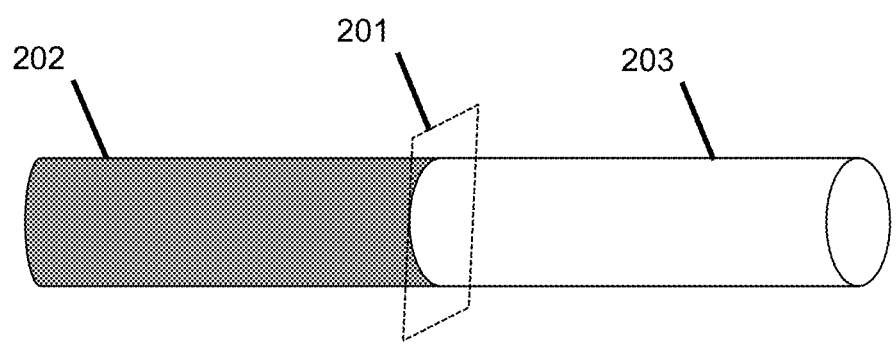
FIG. 2B illustrates segmented with a first visual representation adjustment logic applied to the first portion of the segmented structure and a second visual representation adjustment logic applied to the second portion of the segmented structure.

FIG. 2B illustrates segmented with a first visual representation adjustment logic applied to the first portion of the segmented structure and a second visual representation adjustment logic applied to the second portion of the segmented structure. A digital geometric object 201 is placed across the mis-portion of the blood vessel, which divides the blood vessel into a first portion 202 and a second portion 203. Note that the first portion 202 has a first visual representation adjustment logic applied to it (i.e., note that it is a gray structure). Note that the second visual representation adjustment logic has a second visual representation adjustment logic applied to it (i.e., note that it is translucent). This example includes a blood vessel. Another example would be to place a 2D plane across the kidney to divide it to the upper and lower poles and apply a first visual representation adjustment logic to the upper pole (e.g., shades or red) and a second visual representation adjustment logic to the lower pole (e.g., shades of gray). Thus, a 2D geometric object can be utilized to divide a structure and perform two (or more) different visual representation adjustment logics to a segmented structure. In some embodiments, two (or more) different visual representation adjustment logics could be applied to the different portions of the same structure as assigned by methods including: artificial intelligence; area of anatomy statistically more likely to harbor pathology; and, user preference.

Figure 3:
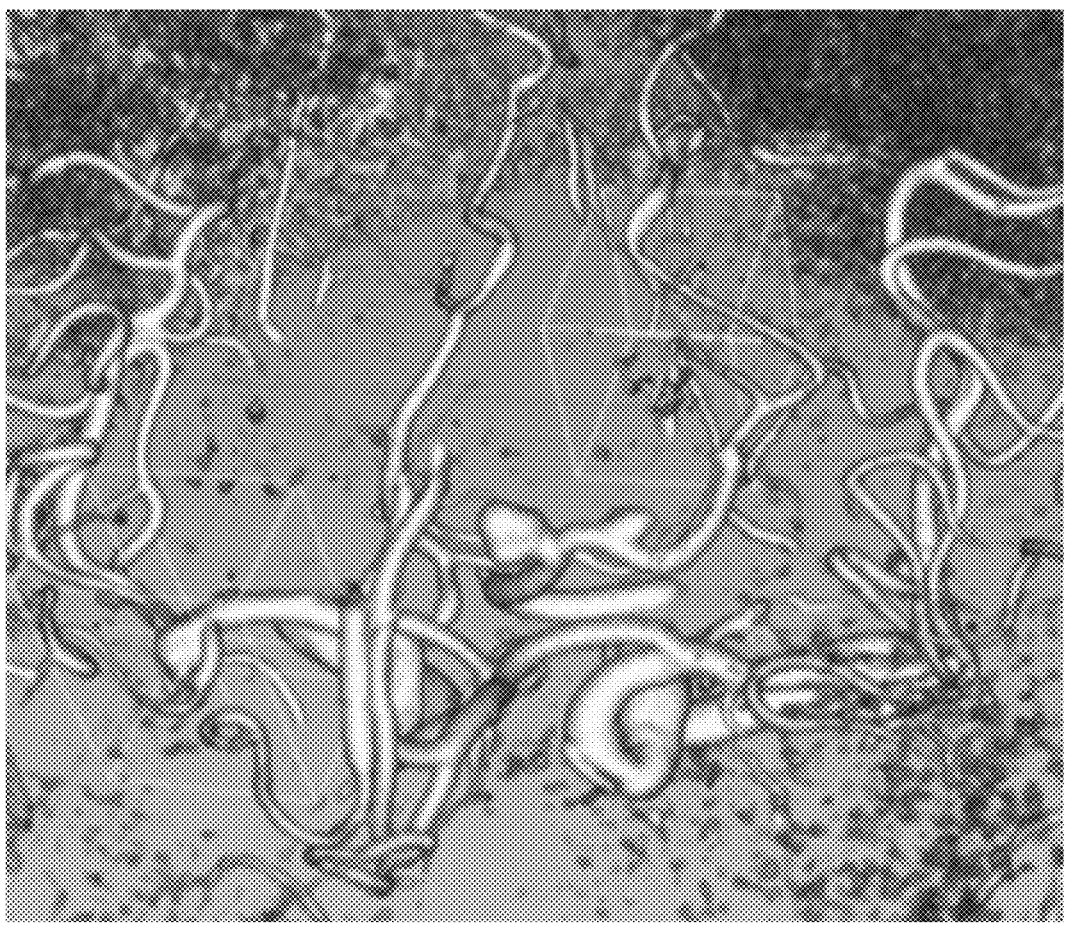
FIG. 3 illustrates the use of a 3D cursor to encase a key feature within the cubelike sub-volume.

FIG. 3 illustrates the use of a 3D cursor to encase a key feature within the cubelike sub-volume. This figure illustrates the cerebrovasculature of an actual patient after certain types of tissues within the cubelike sub-volume have been removed in order to optimize viewing of the cerebrovasculature. In the upper right portion, a 3D cursor (on this 2D picture) is shown encasing a portion of the blood vessels in which there is an aneurysm. The 3D cursor is very flexible: it can be re-sized; re-positioned; and orientation modified. One key feature in this patent is the actual size of the 3D cursor can be measured through the Cartesian Coordinate system which is aligned with the cubelike structure. Also, the volume of the aneurysm can be computed. This can be very useful in cases wherein medical images (e.g., MRI, CT, PET) are obtained over time and changes, if any, can be determined in an aneurysm (or with other abnormalities such as tumors).

Figure 4A:
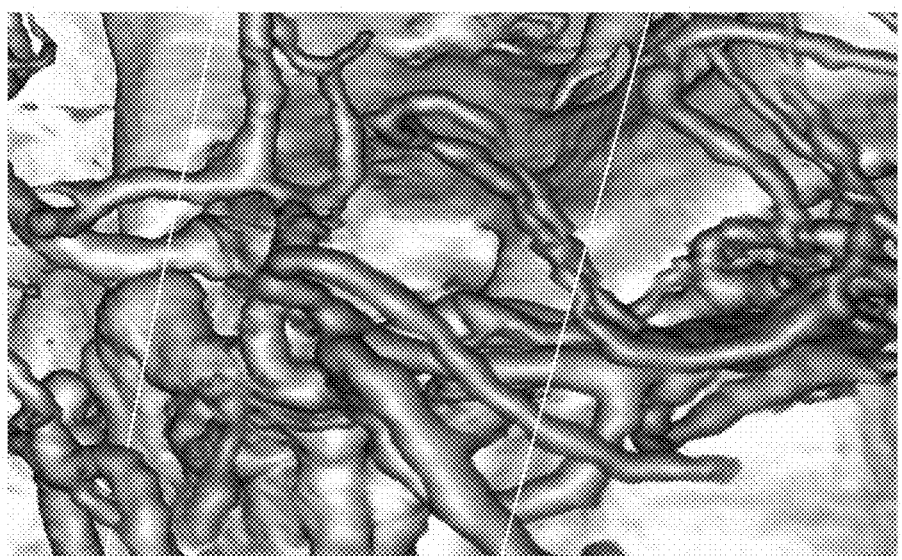
FIG. 4A illustrates the a view point within the cubelike sub-volume wherein the key finding is not identified (false negative).

FIG. 4A illustrates the a view point within the cubelike sub-volume wherein the key finding is not identified (false negative). Note that this viewing angle shows significant overlap of multiple blood vessels. This case caused the observer to miss a brain aneurysm, which is a false negative.

Figure 4B:
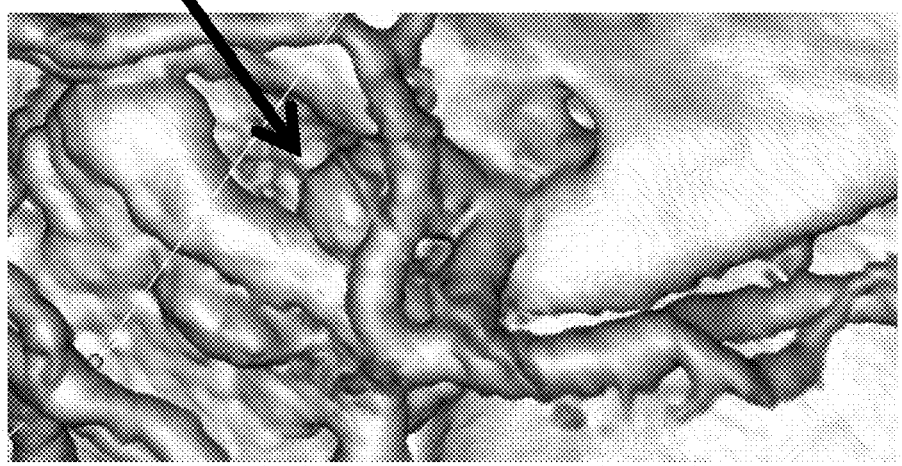
FIG. 4B illustrates the use of optimal observation points within the cubelike sub-volume wherein the key finding is identified (true positive).

FIG. 4B illustrates the use of optimal observation points within the cubelike sub-volume wherein the key finding is identified (true positive). The implementation of optimal viewing angles was performed. As a result, the observer identified a brain aneurysm, which is a true positive. Note that a set of optimal viewing angles is recommended for each structure of interest (e.g., 3 views of the anterior communicating artery). Some of the features of U.S. Pat. No. 8,384,771, METHOD AND APPARATUS FOR THREE DIMENSIONAL VIEWING OF IMAGES, include the capability of the user to change the viewing distance and viewing position of the solid structure. For this patent, there are multiple modes for which these changes can be accomplished: hand control unit, voice commands; and keyboard input. Movement can be continuous or step function. For example, a rotation could slowly change the angular orientation between the user and the solid structure or it could change in 30 degree segments near instantaneously. Also, distinct observation points could be derived over time which give a good view of the region of interest and these points could automatically be changed from one point to another by a 'click' of the handset. This ultimately gives the user a very high probability of detecting anomalies which may otherwise be occluded by some standard view. The methods outlined in this patent caused the aneurysm to be detected, as shown in 400.

FIG. 5 illustrates examples of radiologist checklist items with associated digital geometric objects for sub-volume creation and subsequent visualization techniques implemented. The first example is of the cerebral vasculature. The digital geometric objects include the 6 planes with anatomical landmarks identified by AI algorithm, as disclosed in FIG. 1. The other visualization techniques implemented include application of 2 different visual representation adjustment logics applied to different parts of the same segmented structure (e.g., anterior cerebral arteries non-transparent and all other cerebrovascular structures transparent).

FIG. 6 illustrates techniques for improving analysis of the sub-volume. First, techniques include voxel filtering and stereoscopic rendering and others are incorporated as described by U.S. Pat. No. 8,384,771, METHOD AND APPARATUS FOR THREE DIMENSIONAL VIEWING OF IMAGES, which is incorporated by reference. Next, techniques include convergence and others are incorporated as described by U.S. Pat. No. 9,349,183, METHOD AND APPARATUS FOR THREE DIMENSIONAL VIEWING OF IMAGES, which is incorporated by reference. Next, techniques include the use of alternative head display units and others are incorporated as described by U.S. Pat. No. 9,473,766, METHOD AND APPARATUS FOR THREE DIMENSIONAL VIEWING OF IMAGES, which is incorporated by reference. Next, techniques include the use of a 3D volume cursor and others are incorporated as described by U.S. Pat. No. 9,980,691, METHOD AND APPARATUS FOR THREE DIMENSIONAL VIEWING OF IMAGES, which is incorporated by reference. Next, techniques include the use of an interactive 3D cursor and others are incorporated as described by U.S. patent application Ser. No. 15/878,463, INTERACTIVE 3D CURSOR FOR USE IN MEDICAL IMAGING, which is incorporated by reference. Next, techniques include double windowing and others are incorporated and others as described in U.S. Pat. No. 10,586,400, PROCESSING 3D MEDICAL IMAGES TO ENHANCE VISUALIZATION, which is incorporated by reference. Next, techniques including use of modified segmented structure and others are incorporated as described in U.S. patent application Ser. No. 16/785,606, IMPROVING IMAGE PROCESSING VIA A MODIFIED SEGMENTED STRUCTURE, which is incorporated by reference. Next, techniques including use of double compression mammography and others are incorporated as described in U.S. patent application Ser. No. 16/594,139, METHOD AND APPARATUS FOR PERFORMING 3D IMAGING EXAMINATIONS OF A STRUCTURE UNDER DIFFERING CONFIGURATIONS AND ANALYZING MORPHOLOGIC CHANGES, which is incorporated by reference. Next, techniques including those of smart scrolling and others are incorporated as described in U.S. patent application Ser. No. 16/842,631, A SMART SCROLLING SYSTEM, which is incorporated by reference. Next, techniques of eye tracking are incorporated as disclosed in U.S. Provisional Patent Applications 62/856,185 filed on Jun. 3, 2019 and 62/985,363 filed on Mar. 5, 1920, which are incorporated by reference. Next, techniques of affixing a sub-volume onto a geo-registered tool are incorporated as disclosed in U.S. Pat. No. 10,712,837, USING GEO-REGISTERED TOOLS TO MANIPULATE THREE-DIMENSIONAL MEDICAL IMAGES, which is incorporated by reference. Next, techniques of virtual toolkit and others are incorporated as disclosed in PCT/US2019/036904, A VIRTUAL TOOL KIT FOR 3D IMAGING, which is incorporated by reference. Next, techniques of interaction between geo-registered tools and virtual tools are incorporated as disclosed in U.S. patent application Ser. No. 16/563,985, A METHOD AND APPARATUS FOR THE INTERACTION OF VIRTUAL TOOLS AND GEO-REGISTERED TOOLS, which is incorporated by reference. Next, techniques of prioritized volume rendering are incorporated as disclosed in U.S. patent application Ser. No. 16/879,758, A METHOD AND APPARATUS FOR PRIORITIZED VOLUME RENDERING, which is incorporated by reference. Next, techniques of radiologist assisted machine learning are incorporated as disclosed in PCT/US2019/023968, RADIOLOGIST-ASSISTED MACHINE LEARNING WITH INTERACTIVE, VOLUME-SUBTENDING 3D CURSOR, which is incorporated by reference. Next, techniques of illustrating flow are incorporated as disclosed in U.S. patent application Ser. No. 16/506,073, A METHOD FOR ILLUSTRATING DIRECTION OF BLOOD FLOW VIA POINTERS, and Ser. No. 16/779,658, 3D IMAGING OF VIRTUAL FLUIDS AND VIRTUAL SOUNDS, which are incorporated by reference.

FIG. 7 illustrates text boxes highlighting key aspects in this patent. Text box 700 illustrates examples of digital geometric object include, but are not limited to, the following: a point in space (or a single voxel); a line (straight or curving); a plane (or a curving surface); and, a 3D object (such as a sphere, cube, cube-like structure or cone). Examples of anatomic landmarks include, but are not limited to, the following: specific spots on a bone (e.g., pterion of the calvarium); specific spots on the thyroid gland (e.g., anterior most portion of the isthmus); and, specific spots on the liver (e.g., falciform ligament). Text box 701 illustrates examples contents of sub-volumes include, but are not limited to, the following: an item on a radiologist's checklist (e.g. cerebrovasculature); and, an item that a surgeon is interested in looking at more closely (e.g., kidney which has suffered a laceration and surgeon needs to determine whether he/she can repair it or needs to perform a nephrectomy). Text box 702 illustrates examples of viewing of sub-volumes include, but are not limited to, the following: 2D monitor; and, extended reality display. Text box 703 illustrates examples of usage of artificial intelligence in this process include, but are not limited to, the following: anatomic landmark identification; determining optimal viewing angle; determine optimum implementation of multiple visual representation adjustment logic application (e.g., first image processing technique (non-transparent) is performed on the proximal third of the anterior cerebral artery, second image processing technique (50% transparent) is applied to the middle third of the anterior cerebral artery, third image processing technique (90% transparent) applied to the distal third of the anterior cerebral artery.

Some aspects, features and implementations described herein may include machines such as computers, electronic components, optical components, and processes such as computer-implemented steps. It will be apparent to those of ordinary skill in the art that the computer-implemented steps may be stored as computer-executable instructions on a non-transitory computer-readable medium. Furthermore, it will be understood by those of ordinary skill in the art that the computer-executable instructions may be executed on a variety of tangible processor devices. For ease of exposition, not every step, device or component that may be part of a computer or data storage system is described herein. Those of ordinary skill in the art will recognize such steps, devices and components in view of the teachings of the present disclosure and the knowledge generally available to those of ordinary skill in the art. The corresponding machines and processes are therefore enabled and within the scope of the disclosure.

Throughout the entirety of the present disclosure, use of the articles "a" or "an' to modify a noun may be understood to be used for convenience and to include one, or more than one of the modified noun, unless otherwise specifically stated. Elements, components, modules, and/or parts thereof that are described and/or otherwise portrayed through the figures to communicate with, be associated with, and/or be based on, Something else, may be understood to so communicate, be associated with, and or be based on in a direct and/or indirect manner, unless otherwise stipulated herein. The device(s) or computer systems that integrate with the processor(s) may include, for example, a personal computer(s), workstation(s) (e.g., Sun, HP), personal digital assistant(s) (PDA(s)), handheld device(s) such as cellular telephone(s), laptop(s), handheld computer(s), or another device(s) capable of being integrated with a processor(s) that may operate as provided herein. Accordingly, the devices provided herein are not exhaustive and are provided for illustration and not limitation. References to "a microprocessor and "a processor, or "the microprocessor and "the processor." may be understood to include one or more microprocessors that may communicate in a stand-alone and/or a distributed environment(s), and may thus be configured to communicate via wired or wireless communications with other processors, where such one or more processor may be configured to operate on one or more processor-controlled devices that may be similar or different devices. Use of such "microprocessor or "processor terminology may thus also be understood to include a central processing unit, an arithmetic logic unit, an application-specific integrated circuit (IC), and/or a task engine, with such examples provided for illustration and not limitation. Furthermore, references to memory, unless otherwise specified, may include one or more processor-readable and accessible memory elements and/or components that may be internal to the processor-controlled device, external to the processor-controlled device, and/or may be accessed via a wired or wireless network using a variety of communications protocols, and unless otherwise specified, may be arranged to include a combination of external and internal memory devices, where Such memory may be contiguous and/or partitioned based on the application. Accordingly, references to a database may be understood to include one or more memory associations, where such references may include commercially available database products (e.g., SQL, Informix, Oracle) and also include proprietary databases, and may also include other structures for associating memory Such as links, queues, graphs, trees, with such structures provided for illustration and not limitation. References to a network, unless provided otherwise, may include one or more intranets and/or the Internet, as well as a virtual network. References hereinto microprocessor instructions or microprocessor-executable instructions, in accordance with the above, may be understood to include programmable hardware.

Unless otherwise stated, use of the word "substantially' may be construed to include a precise relationship, condition, arrangement, orientation, and/or other characteristic, and deviations thereof as understood by one of ordinary skill in the art, to the extent that such deviations do not materially affect the disclosed methods and systems. Throughout the entirety of the present disclosure, use of the articles "a" or "an' to modify a noun may be understood to be used for convenience and to include one, or more than one of the modified noun, unless otherwise specifically stated. Elements, components, modules, and/or parts thereof that are described and/or otherwise portrayed through the figures to communicate with, be associated with, and/or be based on, Something else, may be understood to so communicate, be associated with, and or be based on in a direct and/or indirect manner, unless otherwise stipulated herein. Although the methods and systems have been described relative to a specific embodiment thereof, they are not so limited. Obviously many modifications and variations may become apparent in light of the above teachings. Many additional changes in the details, materials, and arrangement of parts, herein described and illustrated, may be made by those skilled in the art. Having described preferred embodiments of the invention it will now become apparent to those of ordinary skill in the art that other embodiments incorporating these concepts may be used. Additionally, the software included as part of the invention may be embodied in a computer program product that includes a computer useable medium. For example, such a computer usable medium can include a readable memory device, such as a hard drive device, a CD-ROM, a DVD ROM, or a computer diskette, having computer readable program code segments stored thereon. The computer readable medium can also include a communications link, either optical, wired, or wireless, having program code segments carried thereon as digital or analog signals. Accordingly, it is submitted that that the invention should not be limited to the described embodiments but rather should be limited only by the spirit and scope of the appended claims.

Several features, aspects, embodiments and implementations have been described. Nevertheless, it will be understood that a wide variety of modifications and combinations may be made without departing from the scope of the inventive concepts described herein. Accordingly, those modifications and combinations are within the scope of the following claims.

What is claimed is:
1. A method comprising:
using a 3D image
wherein said 3D image is obtained from a CT scan, a MRI scan, a PET scan, a SPECT scan or an ultrasound scan, and
wherein said 3D image comprises anatomic structures;
performing segmentation of said 3D image into said anatomic structures,
selecting a first anatomic landmark, a second anatomic landmark, a third anatomic landmark and a fourth anatomic landmark from said anatomic structures wherein said first anatomic landmark, said second anatomic landmark, said third anatomic landmark and said fourth anatomic landmark are different anatomic landmarks;
determining a first 3D coordinate corresponding to said first anatomic landmark, a second 3D coordinate corresponding to said second anatomic landmark, a third 3D coordinate corresponding to said third anatomic landmark and a fourth 3D coordinate corresponding to said fourth anatomic landmark wherein said first 3D coordinate, said second 3D coordinate, said third 3D coordinate and said fourth 3D coordinate are different coordinates; and
generating a digital geometric object within said 3D image wherein a configuration of said digital geometric object is different from said anatomic structures' configurations, wherein a boundary of said digital geometric object is determined by at least said first 3D coordinate, said second 3D coordinate, said third 3D coordinate and said fourth 3D coordinate, and wherein the digital geometric object is used to define a boundary of a sub-volume within the 3D dataset.

2. The method of claim 1 further comprising wherein the digital geometric object consists of one of the group of: a curving surface; and, a 3D object.

3. The method of claim 1 further comprising wherein a first image processing technique is performed on the sub-volume and a second image processing technique is performed on portions of the 3D volume other than the sub-volume.

4. The method of claim 1 further comprising wherein the sub-volume is defined by at least one additional digital geometric object placed in proximity to at least one additional pre-selected anatomic landmark within the 3D dataset.

5. The method of claim 4 further comprising wherein the digital geometric object is connected to the at least one additional digital geometric object to further define the boundary of the sub-volume within the 3D dataset.

6. The method of claim 1 wherein the anatomic landmarks identified by artificial intelligence.

7. The method of claim 1 wherein the segmentation is performed within the sub-volume.

8. The method of claim 1 wherein filtering is performed within the sub-volume.

9. The method of claim 1 wherein the sub-volume is viewed with a 2D monitor or an extended reality display.

10. The method of claim 1 further comprising wherein automatic shape recognition technology is used to identify findings within the sub-volume.

11. The method of claim 1 further comprising wherein the sub-volume is generated for an item in a radiology checklist.

12. The method of claim 1 further comprising wherein the sub-volume is viewed with a prioritized volume rendering imaging technique.

13. The method of claim 1 further comprising wherein the sub-volume is viewed in conjunction with voxel manipulation.

14. The method of claim 1 further comprising wherein the anatomic landmark is named and labeled by an AI algorithm and subsequently displayed to a user.

15. The method of claim 1 further comprising wherein an anatomic feature within the sub-volume is segmented wherein a first portion of the anatomic feature is displayed with a first imaging processing technique and a second portion of the anatomic feature is displayed with a second image processing technique.

16. The method of claim 1 further comprising wherein eye tracking of a user is performed as the user looks at the sub-volume.

17. The method of claim 1 further comprising wherein a modified segmented structure is performed within the sub-volume.

18. The method of claim 1 further comprising wherein analysis of the sub-volume is performed.

19. A non-transitory computer readable medium having computer readable code thereon for image processing, the medium comprising instructions for:

using a 3D image wherein said 3D image is obtained from a CT scan, a MRI scan, a PET scan, a SPECT scan or an ultrasound scan, and wherein said 3D image comprises anatomic structures;

performing segmentation of said 3D image into said anatomic structures, selecting a first anatomic landmark, a second anatomic landmark, a third anatomic landmark and a fourth anatomic landmark from said anatomic structures wherein said first anatomic landmark, said second anatomic landmark, said third anatomic landmark and said fourth anatomic landmark are different anatomic landmarks;

determining a first 3D coordinate corresponding to said first anatomic landmark, a second 3D coordinate corresponding to said second anatomic landmark, a third 3D coordinate corresponding to said third anatomic landmark and a fourth 3D coordinate corresponding to said fourth anatomic landmark wherein said first 3D coordinate, said second 3D coordinate, said third 3D coordinate and said fourth 3D coordinate are different coordinates; and generating a digital geometric object within said 3D image wherein a configuration of said digital geometric object is different from said anatomic structures' configurations, wherein a boundary of said digital geometric object is determined by at least said first 3D coordinate, said second 3D coordinate, said third 3D coordinate and said fourth 3D coordinate, and wherein the digital geometric object is used to define a boundary of a sub-volume within the 3D dataset.

20. A computer system comprising:

a memory; and a processor;

wherein the memory is encoded with an application providing image processing, that when performed on the processor, provides a process for processing information, the process causing the computer system to perform the operations of:

using a 3D image wherein said 3D image is obtained from a CT scan, a MRI scan, a PET scan, a SPECT scan or an ultrasound scan, and wherein said 3D image comprises anatomic structures;

performing segmentation of said 3D image into said anatomic structures, selecting a first anatomic landmark, a second anatomic landmark, a third anatomic landmark and a fourth anatomic landmark from said anatomic structures wherein said first anatomic landmark, said second anatomic landmark, said third anatomic landmark and said fourth anatomic landmark are different anatomic landmarks;

determining a first 3D coordinate corresponding to said first anatomic landmark, a second 3D coordinate corresponding to said second anatomic landmark, a third 3D coordinate corresponding to said third anatomic landmark and a fourth 3D coordinate corresponding to said fourth anatomic landmark wherein said first 3D coordinate, said second 3D coordinate, said third 3D coordinate and said fourth 3D coordinate are different coordinates; and generating a digital geometric object within said 3D image wherein a configuration of said digital geometric object is different from said anatomic structures' configurations, wherein a boundary of said digital geometric object is determined by at least said first 3D coordinate, said second 3D coordinate, said third 3D coordinate and said fourth 3D coordinate, and wherein the digital geometric object is used to define a boundary of a sub-volume within the 3D dataset.

* * * * *